(12) United States Patent
Schilling

(10) Patent No.: US 7,440,855 B2
(45) Date of Patent: Oct. 21, 2008

(54) IDENTIFICATION OF ANTIBIOTIC TARGETS AND CRITICAL POINTS IN METABOLIC NETWORKS BASED ON PATHWAY ANALYSIS

(75) Inventor: Christophe Schilling, San Diego, CA (US)

(73) Assignee: The Regents of the University of California

( * ) Notice: Subject to any disclaimer, the term of this patent is extended or adjusted under 35 U.S.C. 154(b) by 585 days.

(21) Appl. No.: 09/928,191

(22) Filed: Aug. 11, 2001

(65) Prior Publication Data

US 2003/0032576 A1 Feb. 13, 2003

(51) Int. Cl.
*G06F 19/00* (2006.01)
(52) U.S. Cl. .......................................... 702/19
(58) Field of Classification Search .................. None
See application file for complete search history.

(56) References Cited

OTHER PUBLICATIONS

Schilling et al. ((Biotechnol. Bioeng. (2000/2001) vol. 71, pp. 286-306; published online Mar. 30, 2001).*

* cited by examiner

*Primary Examiner*—Lori A Clow
(74) *Attorney, Agent, or Firm*—DLA Piper LLP (US)

(57) ABSTRACT

A computational approach to identifying potential antimicrobial drug targets based on the structural capabilities of the microbe's metabolic network, which may be reconstructed from genomic and biochemical information. Starting with a cellular metabolic network (i) a stoichiometric matrix is generated to describe the connectivity of the reaction in the network, where (ii) constraints can be placed on various fluxes to allow for defined inputs and outputs to the network. For the defined network the unique set of extreme pathways can together be used to describe the complete range of metabolic capabilities of the network. From these pathways, sets of reactions whose elimination from the network removes certain production capabilities from the network can be mathematically determined by process of convex analysis.

11 Claims, 5 Drawing Sheets

Figure 4

Table 1

| Pathway Number | Internal Fluxes | | | | | | | | Exchange Fluxes | | |
|---|---|---|---|---|---|---|---|---|---|---|---|
| | $v_1$ | $v_2$ | $v_3$ | $v_4$ | $v_5$ | $v_6$ | $v_7$ | $v_8$ | $b_1$ | $b_2$ | $b_3$ |
| 1 | | | | | | | | | | | |
| 2 | | | | | | | | | | | |
| 3 | 0 | 0 | 0 | 0 | 3 | 0 | 2 | 1 | 0 | -1 | 1 |
| 4 | 0 | 0 | 0 | 0 | 1 | 2 | 0 | 1 | 0 | -1 | 1 |
| 5 | 4 | 1 | 3 | 0 | 0 | 0 | 2 | 1 | -4 | 0 | 1 |
| 6 | 4 | 3 | 1 | 0 | 0 | 2 | 0 | 1 | -4 | 0 | 1 |
| 7 | 4 | 4 | 0 | 0 | 3 | 0 | 2 | 1 | -4 | 0 | 1 |
| 8 | 4 | 4 | 0 | 0 | 1 | 2 | 0 | 1 | -4 | 0 | 1 |
| 9 | 0 | 0 | 1 | 1 | 0 | 0 | 0 | 0 | 0 | 0 | 0 |
| 10 | 0 | 1 | 0 | 1 | 1 | 0 | 0 | 0 | 0 | 0 | 0 |

Table 1: The set of extreme pathways (p1,...,p10) for the reaction scheme depicted in Figure 2. Pathway 1 and 2 correspond to pathways utilizing both metabolite A and C as substrates, while pathway 3 and 4 utilize only metabolite C. Pathway 5, 6, 7, and 8 utilize metabolite A as the sole substrate. Pathway 9 and 10 show no activity in the exchange fluxes and correspond to internal cycles.

IDENTIFICATION OF ANTIBIOTIC TARGETS AND CRITICAL POINTS IN METABOLIC NETWORKS BASED ON PATHWAY ANALYSIS

BACKGROUND OF THE INVENTION

1. Field of the Invention

The present invention generally concerns the identification of (i) pathways and (ii) critical points in, and (iii) the generation of mathematical models of, existing and proposed cellular metabolic networks comprised of biochemical reactions or mechanisms with genetic or non-genetic associations.

More specifically, the present invention relates to computational methods and systems for the analysis and modeling of cellular metabolic networks so that, inter alia, potential targets in support of the directed development of therapeutic agents and engineered microbial strains may be identified.

2. Description of the Prior Art

2.1 General Background

Within a cell of any organism there are complicated networks of interacting proteins and enzymes that perform certain chemical conversions and transformations. These conversions and transformations—life processes—ultimately lead to the production of the (i) necessary building blocks (biomass constituents such as amino acids, nucleotides, phospholipids, etc.) and (ii) energy requirements of the cell. Environmental substances are processed to meet the demands of a living cell through this the cell's network of biochemical reactions.

These biochemical reaction networks primarily involve the use of enzymes derived from particular genes whose chromosomal location and function have been characterized, as well as enzymes inferred to be present based on similarity of their genomic sequence to the genomic sequences of enzyme-coding genes in other organisms. There is presently, circa 2000, much focus on attempting to model and to 'reconstruct' these networks of a living organism based, primarily, on the use of genome sequence information of the organism.

Meanwhile, the arsenal of reactions that a cell has at its disposal dictate the production capabilities and maximal performance characteristics of the cell. To change these capabilities the cell would have to acquire new biochemical reactions through some evolutionary mechanism. In so doing the cell would of necessity increase the range of feasible routes by which it could meet certain cellular demands from a set of environmental supplies.

2.2 The Utility of Mathematics to Analyze Biochemical Reaction Networks

The capabilities of cellular biochemical reaction networks (i) to produce necessary building blocks and energy requirements, and (ii) to evolve the reaction pathways by which cellular production(s) is (are) realized, can be comprehensively examined using rigorous mathematics. Mathematical examination yields results which are biochemically meaningful, serving to predict the performance of the biochemical reaction network.

There exists one particular type of mathematical analysis of cellular biochemical reaction networks called "convex analysis". need definition. Some of the principles of convex analysis were previously used by Schuster to find "elementary nodes", or reactions within the biochemical reaction networks. See Schuster, S., T. Dandekar and D. A. Fell, 1999, Detection of elementary flux modes in biochemical networks: a promising tool for pathway analysis and metabolic engineering, *Trends Biotechnology* 17(2): 53-60. See also Schuster, S. and C. Hilgetag, 1994, On elementary flux modes in biochemical reaction systems at steady state. *J. Biological Systems* 2(2): 165-182. Finally see Schuster, S., C. Hilgetag, J. H. Woods and D. A. Fell, 1996, Elementary modes of functioning in biochemical networks.

Convex analysis was also previously used by Bruce Clarke to find "extreme currents", or reaction pathways through the biochemical reaction networks by which pathways the biochemical reaction networks succeed in processing environmental substances into the building blocks and energy requirements of the cell. See Clarke, B. L., 1980, Stability of Complex Reaction Networks. *Advances in Chemical Physics* 43: 1-215. See also Clarke, B. L., 1981, Complete set of steady states for the general stoichiometric dynamical system. *J. Chem. Phys.* 75(10): 4970-4979.

The mathematics associated with convex analysis may be used to determine the minimal set of biochemical pathways by which some particular capability of the biochemical reaction network is realized. These pathways satisfy both (i) mass balance constraints (associated with stoichiometry) and (ii) directional constraints placed on reactions (associated with thermodynamics).

These pathways are termed "extreme pathways", and can beneficially be used to examine the functional capabilities of a biochemical reaction network. Importantly, from knowledge of these extreme pathways it is possible to determine all of the possible combinations of reactions that need to be eliminated from the network to remove some particular capability(ies) of the network. From the lists of reactions it is a simple step to determine the enzymes and genes responsible for these reactions.

Consider now that the elimination of these genes should then render the biochemical reaction network incapable of reaching some particular outcome, some particular demand(s) of the cell!

Conversely, once it is understood what a biochemical reaction network is doing, and how it is doing it, then it may become possible to "re-engineer" the network, and the organism, to steer more of its output into desired channels (i.e., to make more of a desired reaction product).

Mathematical tools that permit recognition of pathways within biochemical reaction networks, and of the genes involved with the reactions within these pathways, have still further implications for the development of antibiotics to combat microbial infections. The tools permit recognition of how a deleterious process and pathway of the biochemical reaction network might be stopped, or at least disrupted.

Alternatively, the same mathematical computational tools can be used to improve the design and engineering of organisms for industrial application such as the production of biocommodities. The tools permit recognition of how an beneficial process and pathway of the biochemical reaction network might be augmented or accentuated.

2.3 Specific Prior Art Mathematical Analysis of Biochemical Reaction Networks Convex analysis has been previously used to study biochemical systems and to generate related sets of pathways called elementary modes and extreme currents. For a comprehensive review see the paper by inventor of the present invention Schilling and his colleagues, see Schilling, C. H., S. Schuster, B. O. Palsson and R. Heinrich, 1999, Metabolic pathway analysis: basic concepts and scientific applications in the post-genomic era. *Biotechnology Progress* 15(3): 296-303.

Elementary modes have been used to metabolically engineer bacteria for producing aromatic amino acid precursors at yields near the maximum theoretical yield. See Liao, J. C., S-Y Hou and Y-P Chao, 1996, Pathway Analysis, Engineering, and Physiological Considerations for Redirecting Central Metabolism.

Liao, et al., report research where all of the elementary modes for a reduced reaction network in *Escherichia coli* were calculated and studied to determine the optimal flux distributions through a central metabolism that redirected carbon flow to the pathways from aromatic amino acid production. Reactions that did not appear in the optimal pathways were considered indispensable, while those that did appear in the optimal pathways were candidates for overexpression.

A similar analysis can be performed with the extreme pathways rather than elementary modes. For the precise difference between these two approaches see Schilling, C. H., D. Letscher and B. O. Palsson, 2000, Theory for the systemic definition of metabolic pathways and their use in interpreting metabolic function from a pathway-oriented perspective. *Journal of Theoretical Biology* 203(3): 229-248.

Still other papers and publications discuss the complex analysis of biochemical reaction networks. See (i) Clarke, B. L. 1980, Stability of Complex Reaction Networks, *Advances in Chemical Physics* 43: 1-215; (ii) Clarke, B. L., 1981, Complete set of steady states for the general stoichiometric dynamical system, *J. Chem. Phys.* 75(10): 4970-4979; (iii) Edwards, J. S., R. Ramakrishna, C. H. Schilling and B. O. Palsson, 1999, Metabolic flux balance analysis, (iv) Metabolic Engineering, S. Y. Lee and E. T. Papoutsakis, New York, Marcel Decker, Inc.: 13-58; (v) Liao, J. C., S-Y Hou and Y-P Chao, 1996, Pathway Analysis, Engineering, and Physiological Considerations for Redirecting Central Metabolism, *Biotechnology and Bioengineering* 52: 129-140; (vi) Schilling, C. H., S. Schuster, B. O. Palsson and R. Heinrich, 1999, Metabolic pathway analysis: basic concepts and scientific applications in the post-genomic era. *Biotechnology Progress* 15(3): 296-303; (vii) Schuster, S., T. Dandekar and D. A. Fell, 1999, Detection of elementary flux modes in biochemical networks: a promising tool for pathway analysis and metabolic engineering, *Trends Biotechnology* 17(2): 53-60; (viii) Schuster, S. and C. Hilgetag, 1994, On elementary flux modes in biochemical reaction systems at steady state, *J. Biological Systems* 2(2): 165-182; (ix) Schuster, S., C. Hilgetag, J. H. Woods and D. A. Fell, 1996, Elementary modes of functioning in biochemical networks; (x) Computation in Cellular and Molecular Biological Systems, R. Cuthbertson, M. Holcombe and R. Paton, London, World Scientific: 151-165; and (xi) Varma, A. and B. O. Palsson, 1994. Metabolic Flux Balancing: Basic concepts, Scientific and Practical Use. *Bio/Technology* 12: 994-998.

SUMMARY OF THE INVENTION

The present invention contemplates improvements to the existing mathematical method of convex analysis for purposes of analyzing the production of one or more selected metabolites of a biochemical reaction network so producing metabolites. In simple terms, the improved mathematical method of the present invention explains why a biochemical reaction network—also known as a cellular metabolic network—does what it does. The utility of so knowing is, of course, that precision understanding of the processes of nature best supports the effective, useful and safe manipulation of these processes. For example, a biochemical process inducing disease may sometimes usefully be stopped; a biochemical process producing a valuable biochemical as an metabolic output may sometimes usefully be enhanced.

The present invention contemplates still more than gaining knowledge of a biochemical reaction network: the present invention further contemplates an improved application of the mathematical process of convex analysis particularly for the purpose of identifying critical points in cellular metabolic networks engaging in biochemical reactions. The improved analysis proceeds so that, by identification of some critical point, all members of the particular set of complex pathways of biochemical reactions leading to this point may be better understood. The better understanding this set of complex pathways again permits the better understanding of which reactions, and associated reaction pathways, can either be (i) disrupted so as to defeat that the cellular metabolic network should attain this critical point, or (ii) enhanced, so that the cellular metabolic network will produce more of some selected biochemical(s) at the critical point, and/or produce this biochemical (these biochemicals) faster. In simple possible terms, the improved mathematical method of the present invention not only explains how a biochemical reaction network, or cellular metabolic network, functions (as in the preceding paragraph), but permits analysis of why and how the network might be (i) precluded or obstructed from working (as in the avoidance of disease), or, alternatively (ii) made to work better and/or faster (as in the production of a useful biochemical product).

The present invention contemplates yet still more: an improved method of deriving a mathematical system of linear equations and linear inequalities representing—i.e., serving as a mathematical model of—a biochemical reaction network (also known as a metabolic network) in other that the derived system may be rigorously analyzed. Improvements to the existing mathematical process of convex analysis are again involved. In simplest possible terms, the present invention delivers more than just a "road map" to biochemical life processes (as in the second preceding paragraph), or even a "road map" with all major "way points" prominently accurately identified (as in the immediately preceding paragraph), but actually delivers a mathematical model of the biochemical reactions of a metabolic network which mathematical model quantitatively captures the production capabilities of the network.

Clearly such knowledge of what is produced, by what processes, when, and to what amount(s) starts to subject life processes—as are conducted by cellular metabolic networks engaging in biochemical reactions—to the techniques of (bio)chemical engineering. One the (bio)chemical "plant" and its processes are understood, then a (bio)chemical engineer should, and is, able to approach modification of the "plant" and/or its (life) processes in order to obtain different, or better, results.

1. General Approach of the Present Invention

The present invention provides a general framework and system for the identification of all the minimal sets of reactions that, when removed from a biochemical reaction network, will render the network unable to reach its particular production objectives.

As precursor steps to the present invention, biochemical reaction networks are conventionally (i) constructed from genomic and biochemical data and (ii) described by a stoichiometric matrix. Together, the constraints on the directions in which reactions can proceed and the stoichiometric matrix correspond to a mathematical system of linear equations and linear inequalities, which system can be studied using convex analysis.

In accordance with the present invention, sets of extreme pathways are defined that are used to represent all of the possible steady states which the network can achieve. By removing a single reaction in the network all of the pathways that utilize this reaction are also removed. To remove the ability of the network to reach a particular objective, all of the extreme pathways that reach this objective must be removed.

In one embodiment of the invention, a set of reactions and their associated genes are identified that will eliminate the ability of the target organism to generate essential biomolecules necessary for its growth.

Rather than removing one reaction at a time—or many reactions at a time—in order to determine the effects of the removal(s) on the performance of the reaction network, it is ideal to be able to calculate all of the sets of reactions that will eliminate the capability of the network to achieve a particular production objective. In an additional embodiment of the invention, an algorithm is presented by which it is possible to generate the entire group of sets of reactions that can be used to eliminate functional properties and network capabilities of interest in a target organism. Collectively this group of reaction sets will be called "minimal deletion sets".

These deletion sets are unique to the present invention, and quite valuable. They may be, for example, used to identify reactions which are critical to the performance of the network under a particular condition, but whose function is essentially redundant under other conditions. In addition to finding global deletion sets that are critical under all conditions it is then possible to find environmental or condition-specific deletion sets.

In summary, beginning with an advanced, but conventional, stoichiometric matrix and a set of general reaction constraints, the present invention shows how to generate (i) the set of extreme pathways along with (ii) the process for identifying a minimal deletion sets from these pathways. An (iii) algorithm is then shown by application of which algorithm all the minimal deletion sets in the network may be may be identified.

These mathematical processes of the present invention, as discussed in greater detail hereinafter, are normally embodied in a computer software program. The program can be used to calculate the extreme pathways and minimal deletion sets of a biochemical reaction network of virtually any complexity. These valuable minimal deletion sets can then be used, for example, in the subsequent development of drugs to combat infectious disease. They may alternatively be used for the rational design and engineering of organisms for the production of biomolecules of interest (often referred to as metabolic engineering).

2. A Method of Analyzing the Production of One or More Selected Metabolites of a Biochemical Reaction Network Producing Metabolites Accordingly, in one of its aspects the present invention is embodied in an improvement to an existing method of analyzing the production of one or more selected metabolites of a biochemical reaction network that produces metabolites.

The existing method has as inputs (i) reactions of the biochemical reaction network constructed from genomic and biochemical data, (ii) exchange fluxes on such of the produced metabolites as are of interest as inputs and outputs to the network, (iii) a stoichiometric matrix, developed from the reactions in consideration of the exchange fluxes, defining participation of each network metabolite in each reaction and exchange flux of the network, and (iv) a system of linear equations and inequalities mathematically defining the network. From these inputs the existing method serves to identify deletion sets of reactions that, when removed from the network, eliminate the capability of the network to produce a selected metabolite.

In particular, the improvement to this existing method in accordance with the present invention uses the linear equations and inequalities of the network to mathematically calculate a convex solution space called a "flux cone". The calculating produces "generating vectors" of this flux cone, which generating vectors are called "extreme pathways". Using these generating vectors (called extreme pathways), the mathematical process of the present invention continues to determine sets of reactions that, when deleted, diminish or eliminate capability of the network to produce an output metabolite of interest.

These mathematically determined sets correspond to critical reactions of the network which, when stopped, affect the capability of the network to produce the output metabolite of interest.

The method of the present invention may, after the determining of sets of reactions, optionally continue with selecting from the determined sets of reactions those sets that totally eliminate the capability of the network to produce the output metabolite of interest. In this case the selected sets are called "deletion sets" because deletion of the reactions represented by the pathways of these sets suffices to totally eliminate the production of the output metabolite of interest by the network.

The calculating of the generating vectors of the flux cone preferably ensues by specific mathematical manipulations within the more general mathematical process of convex analysis. More particularly, the specific preferred convex analysis of the present invention consists of calculating any of (i) a conical basis, (ii) a convex basis, (iii) a linear basis, or (iv) a combination of any of conical and convex and linear bases.

Preferably in the method of the present invention at least some of the constructed reactions will have an associated constraint upon the direction in which the reaction can proceed.

The method of the present invention may be used, for example, to produce an output of interest which consists of one or more functional properties of interest in the analyzed biochemical production network. In this case the reaction sets show how these one or more functional properties of interest can be diminished or eliminated. If the output of interest consists of, for example, but one single functional property of interest in the analyzed biochemical production network then the reaction sets show how this functional property of interest can be diminished or eliminated.

For example, that biochemical reaction network which is analyzed by the mathematical method of the present invention can represent a disease-producing, pathogenic, organism. The metabolite of interest will be one that is necessary for survival of the pathogenic organism. In this situation the method of the present invention using the reaction set can be directed to targeting development of a drug that, by obstructing those reactions of the pathogenic organism that produce the metabolite necessary for survival of the organism, serves to eliminate the pathogenic organism.

As another example, the biochemical reaction network that is analyzed can again represent a disease-producing, pathogenic, organism. However, this time the metabolite of interest can be the actual disease-producing, deleterious, substance that is produced by the pathogenic organism. In this situation the method of the present invention using the reaction set can be directed to targeting the development of a drug that, by obstructing those reactions of the pathogenic organism that produce the metabolite that induces disease, serves to eliminate the deleterious, disease-causing, function of the pathogenic organism.

As an oppositely-directed example, when the reaction network analyzed is an organism producing both desired bio-molecules of value and un-desired bio-molecules of no value, and when the metabolite of interest produced by the organism is defined to be the un-desired and valueless bio-molecules, then the method of the present invention using the reaction set can be directed to metabolically re-engineering the organism to fail of those reactions that produce the particular metabolite that is un-desired and valueless. Thus production of un-desired valueless bio-molecules can be eliminated while continued production of desired valued bio-molecules is permitted.

Similarly to this example, when the reaction network analyzed is an organism producing desired bio-molecules of value by each of two or more—multiple—metabolic routes, and when the metabolite of interest is defined to be the valued molecule as is produced by one only—preferred—route of the multiple routes by which the organism is capable of producing this molecule, then the method of the present invention using the reaction set can be directed to metabolically re-engineering the organism to fail of those reactions that produce the metabolite of interest via inefficient route(s), therein by eliminating production of metabolite via this route (these routes) nonetheless that the metabolite is of value. Production of the desired metabolite by one or more alternative one(s) of the multiple metabolic routes is left intact, and may even be accentuated.

These combinations show the reaction set produced by the mathematical method of the present invention to be a valuable tool. In simple terms, the reaction set shows how to preclude, or to obstruct, or to accentuate individual biochemical pathways within the organism as lead to the production of particular metabolites. It is hard to ask for more than this: a complete quantitative, mathematical, model as to the biochemical reactions of the cell.

3. A Method of Identifying Critical Points in Cellular Metabolic Networks Engaging in Biochemical Reactions In another of its aspects the present invention is embodied in a method of (i) applying in an improved way the existing mathematical process of convex analysis so that a convex hull is defined and spanned by unique generating, or edge, vectors, this hull being analyzed to derive a particular solution that is, mathematically, a particular point described by a flux vector lying within the interior of the convex hull. All this effort to get to this particular solution is for the purpose of (ii) identifying critical points in cellular metabolic networks engaging in biochemical reactions so that, by identification of some critical point, the particular set of complex pathways of biochemical reactions leading to this point may be better understood. All this effort to get to the understanding of all the biochemical reactions leading to a particular point is so that, (iii) by better understanding this set of complex pathways, it may further be better understood which reactions, and associated pathways, can be selectively disrupted so as to defeat that the cellular metabolic network should attain this critical point.

The method of the present invention thus consists of using this convex hull—a mathematical construction—to represent the capabilities of a metabolic genotype. By this usage the unique generating, edge, vectors that define and that span the convex hull represent systemically independent extreme pathways of the metabolic, life, processes of the metabolic genotype.

Likewise in this usage every point in the hull is some non-negative combination of the unique generating, edge, vectors corresponding to the fact that every metabolic, life, process of the metabolic genotype is some combination of the extreme pathways of these metabolic processes.

Next in the method of the present invention, the convex hull is mathematically solved, again by a specific application of the more general process of convex analysis, so as to derive a particular solution that represents a metabolic phenotype. This particular solution is, mathematically, a particular point described by a flux vector lying within the interior of the convex hull.

The mathematical solving is repeated until a complete set of particular solutions, corresponding to a set of flux vectors each lying within the convex hull, is derived. This set of solutions corresponds to all the pathways by which a particular metabolic phenotype is realized.

Thus the derivation of all pathways by which the particular metabolic phenotype is realized is tantamount to recognition of all the biochemical reactions that, as part of any pathways, lead to the particular metabolic phenotype. Moreover, recognition of all biochemical reactions variously leading to the particular metabolic phenotype permits better understanding of what biochemical reactions of the metabolic genotype can be in particular disrupted so as to cause that the metabolic genotype should be unable to realize the particular solution.

For example, this the method of the present invention can be employed on the genotype of a pathogenic, disease-causing, organism. In this case the method of the present invention preferably continues with the development of drugs that, by obstructing those biochemical reactions of the genotype of the pathogenic organism that lead to a particular, disease-inducing, solution of the genotype, serve to eliminate the deleterious, disease-causing, phenotype of the pathogenic organism.

For example, this the method of the present invention can be employed on the genotype of an organism producing both (i) desired bio-molecules of value and (ii) undesired bio-molecules of no value. In this case the method of the present invention preferably continues with metabolically re-engineering the organism so as to obstruct those biochemical reactions of the genotype of the pathogenic organism that lead to that particular solution where the phenotype produces the undesired valueless bio-molecules, eliminating production of these undesired valueless bio-molecules while permitting continued production of desired valued bio-molecules.

4. A Method of Analyzing a Metabolic Network

In still another of its aspects the present invention is embodied in a method of analyzing a metabolic network.

The method consists of first identifying all biochemical reactions occurring in the metabolic network, including any directions thereof. Then all exchange fluxes are specified, including any associated directional restraints attendant upon metabolites of the identified biochemical reactions.

A stoichiometric matrix where each column in the matrix corresponds to a reaction, or flux, and where each row corresponds to a different metabolite involved in the metabolic network is next created. This created stoichiometric matrix represents, in all its columns and rows, the collective biochemical reactions, being a form of chemical conversion, and the collective cellular transport processes of the metabolic network, which cellular transport processes are how the metabolites enter and leave the metabolic network.

All directional constraints on the exchange fluxes are next combined with the created stoichiometric matrix to define the metabolic network as a system of linear equations and linear inequalities.

Finally the system of linear equations and linear inequalities that jointly define the metabolic network are analyzed by the mathematical process of convex analysis.

The metabolic network defined as a system of linear equations and linear inequalities may particularly obeys the three equations $$S \cdot v = 0 \quad \text{(Equation 1)}$$

where S refers to the stoichiometric matrix of the system and v is the flux vector;

$$v_i \geq 0, \forall i \quad \text{(Equation 2)}$$

where $v_i$ corresponds to the flux value of the $i^{th}$ reaction; and $$\alpha_i \leq b_i \leq \beta_i \quad \text{(Equation 3)}$$

where $\alpha_i$ and $\beta_i$ are ether zero of negative and positive infinity, respectively, based on the direction of exchange flux, and $b_i$ corresponds to the $i^{th}$ exchange flux.

In this case the analyzing consists of solving the equations 1-3 in convex space as a convex polyhedral cone in n-dimensional space emanating from the origin of the space.

Every point on the convex polyhedral cone may in particular be represented by $$C = v : v = \sum_{i=1}^{k} \omega_i p_i, \omega_i \geq 0 \forall i \quad \text{(Equation 4)}$$

In this case the analyzing consists of calculating the conical hull of the flux cone as representing the extreme pathways in the metabolic network.

After this calculating (which is a part of the analyzing), the method may further continue by determining from the calculated pathways critical biochemical reactions, or sets of biochemical reactions, that are required for the metabolic network to attain a particular objective or group of objectives— as is (are) represented by one or more particular points on the flux cone.

These and other aspects and attributes of the present invention will become increasingly clear upon reference to the following drawings and accompanying specification.

BRIEF DESCRIPTION OF THE DRAWINGS

Referring particularly to the drawings for the purpose of illustration only and not to limit the scope of the invention in any way, these illustrations follow:

FIG. 3(a) shows a hypothetical reaction network comprised of a series of internal and exchange fluxes, functioning to generate appropriate ratios of metabolites C, D, and E for incorporation into biomass represented as the GRO metabolite;

FIG. 3(b) shows a mathematical translation of the reaction network into the steady-state mass balances and constraints placed on all fluxes that define the solution domain; and FIG. 3(c) is a list of the ten (10) extreme pathways calculated for the network shown in vector format indicating the relative flux activity of each of the fluxes in the pathways.

FIG. 4 is a table 1 showing the set of extreme pathways *p1, ..., p10) for the reaction scheme shown in FIG. 3.

DESCRIPTION OF THE PREFERRED EMBODIMENT

Figure 1:
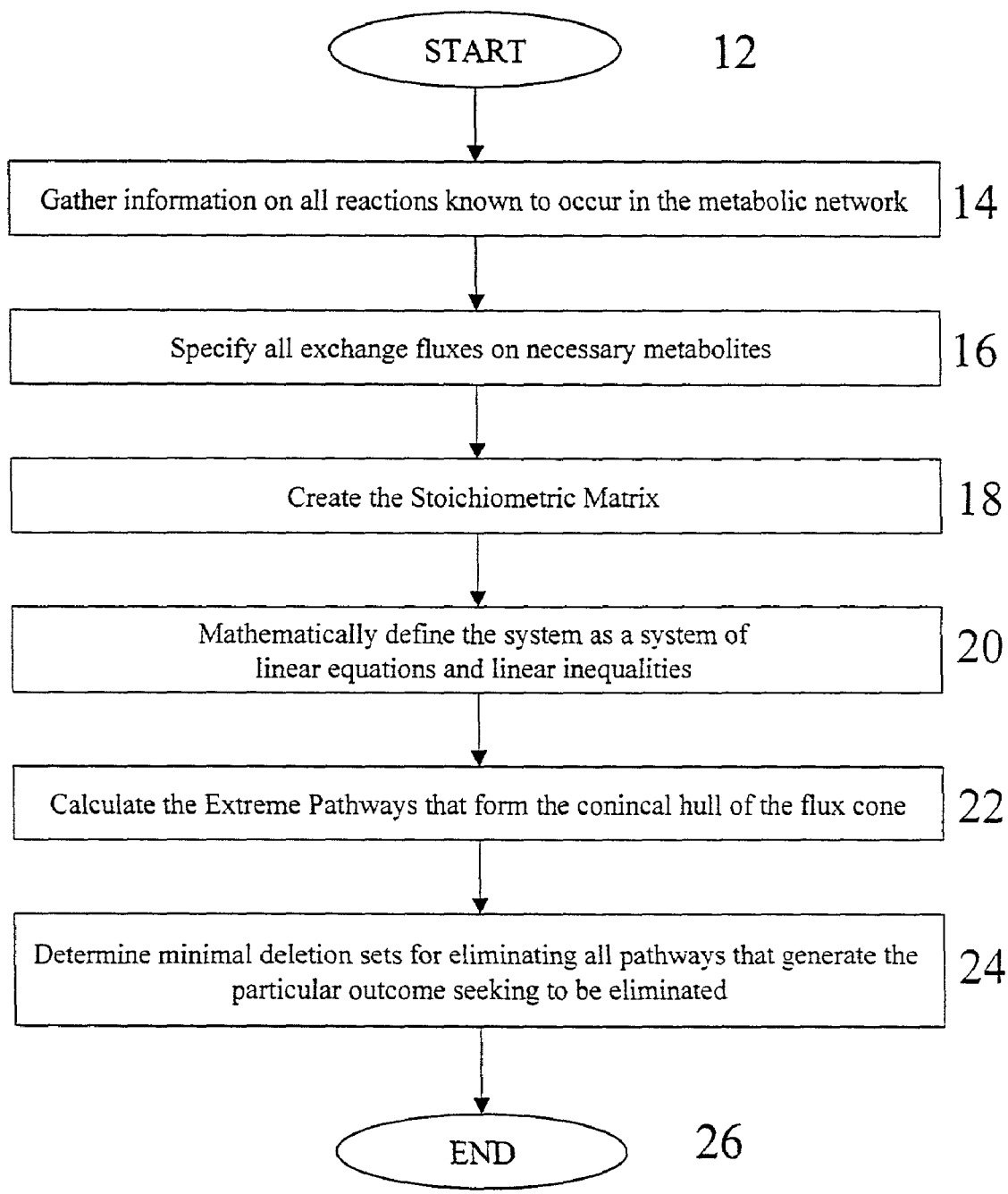
FIG. 1 is a flow diagram illustrating one procedure of the present invention for determining one set, or the entire collection, of minimal deletion sets that eliminate particular production capabilities of interest in a metabolic network.

Although specific embodiments of the invention will now be described with reference to the drawings, it should be understood that such embodiments are by way of example only and are merely illustrative of but a small number of the many possible specific embodiments to which the principles of the invention may be applied. Various changes and modifications obvious to one skilled in the art to which the invention pertains are deemed to be within the spirit, scope and contemplation of the invention as further defined in the appended claims.

The present invention relates to systems and methods for (i) identifying deletion sets in a target organism's metabolic network (ii) based on a pathway analysis (iii) mathematically derived from (iv) a list of reactions associated with convexity, which reactions are a partial or a complete representation of reactions in a cell.

A stoichiometric matrix is used to describe the connectivity amongst all the metabolites in a metabolic network of any complexity including that for an entire organism. Additional constraints on the direction in which reactions and fluxes can proceed in the network serve to complete the mathematical description of the reaction network. From this description existing algorithms can be used to calculate the set of extreme pathways that form the conical hull of the solution space, corresponding to all feasible steady state flux distributions. The details of performing the construction of a stoichiometric matrix and the formulation of the constraints imposed on a biochemical reaction network have been previously disclosed along with an algorithm for calculating the set of extreme pathways (Schilling, 2000). From these pathways it is possible to identify sets of reactions that upon removal from the network eliminate the ability of the network to achieve selected objective of interest. Moreover, it is possible to calculate all of these deletion sets using one algorithm that operates on the set of extreme pathways. These minimal deletion sets may be useful for the identification and development of potential protein and genetic targets for anti-microbial drugs and the engineering of microbial strains for bioproduction purposes.

It should be noted that the systems and methods described herein can be implemented on any conventional host computer system, such as those based on Intel® microprocessors and running Microsoft Windows operating systems. Other systems, such as those using the UNIX or LINUX operating system and based on IBM®, DEC® or Motorola® microprocessors are also contemplated. The systems and methods described herein can also be implemented to run on client-server systems and wide-area networks, such as the Internet.

Software to implement the system can be written in any well-known computer language, such as Java, C, C++, Visual Basic, FORTRAN or COBOL and compiled using any well-known compatible compiler.

The software of the invention normally runs from instructions stored in a memory on the host computer system. Such a memory can be a hard disk, Random Access Memory, Read Only Memory and Flash Memory. Other types of memories are also contemplated to function within the scope of the invention.

The process 10 for determining all minimal deletion sets for any metabolic network of interest is shown in FIG. 1. Beginning at a start state 12, the process 10 then moves to a state 14 to gather all of the known biochemical information pertaining to the reactions in the network. This generates a list of all the chemical reactions occurring in the network. This provides the stoichiometry of each chemical reaction proposed to occur in the network along with information regarding the irreversible and reversible nature of the reactions. The stoichiometry of each reaction provides the molecular ratios in which reactants are converted into products. These reactions include all transport reactions, enzymatic reactions, and diffusion processes. For an entire organism these reactions are catalyzed by gene products whose potential presence in the organism can be inferred from the annotated genome sequence of an organism along with additional biochemical information. Thus the reactions determined in state 14 represent all of the physical-chemical conversions that can reasonably occur in the system.

A theoretical system boundary can be drawn around all of the physically occurring reactions and associated substrates and products defined in state 14. These reactions contained within the system boundary will be collectively referred to as the internal fluxes of the system. The entire group of substrates and products are collectively referred to as the metabolites of the system. The process 10 then moves to a state 16 wherein all of the exchange fluxes are specified in the system. These exchange fluxes will constitute the presence of potential sources and/or sinks on individual metabolites. Therefore if a particular metabolite is to be allowed to enter the system or exit the system an exchange flux is created to allow for the passage of the metabolite across the theoretical system boundary. Conceptually these fluxes can be thought of as the input and outputs of the system and can be defined by the researcher to simulate environmental conditions of interest.

The information obtained in state 14 and 16 regarding the reactions and metabolites participating in the system must be translate into a mathematical format to facilitate the remainder of the process 10. While reversible reactions may be represented as one reaction, for ease of calculation all reactions that are reversible will be decomposed into a forward reaction and a backward reaction that are constrained to only proceed in one positive direction. Therefore all internal fluxes will be constrained to take on only positive values representing their activity levels. Exchange fluxes that serve as both input and outputs for a particular metabolite may also be decomposed in a similar fashion or remain bi-directional, thus capable of taking on any real value (positive and negative). All of the information regarding the internal fluxes, exchange fluxes, and their substrates and products can be represented in a matrix format typically referred to as a stoichiometric matrix. Each column in the matrix corresponds to a given reaction or flux, and each row corresponds to the different metabolites involved in the system. Thus, a given position in the matrix describes the stoichiometric participation of a metabolite (listed in the given row) in a particular flux of interest (listed in the given column). Together all of the columns of the stoichiometric matrix represent all of the chemical conversions and cellular transport processes that are determined to be present in the network. This includes all internal fluxes operating within the system and exchange fluxes operating on the system as inputs and outputs. Thus, the process moves to a state 18 in order to formulate all of the fluxes into a stoichiometric matrix.

Next, the process 10 moves to a state 20 wherein information regarding the directional constraints placed on the fluxes is combined with the stoichiometric matrix to fully define the metabolic network as a system of linear equations and linear inequalities to be analyzed using principles of convex analysis. In studying metabolic networks the principle of conservation of mass is applied in the generation of transient mass balances around each metabolite in the system. Each mass balance constitutes a differential equation describing the change in concentration of the metabolite as function of the activities of the fluxes that serve to generate and dissipate the metabolite. Structural aspects of a metabolic network are time invariant allowing the functioning of the network to be placed into a steady state. Eliminating all the time derivatives obtained from dynamic mass balances around every metabolite in the metabolic system, yields the system of linear equations represented in matrix notation, $$S \cdot v = 0 \quad \text{(Equation 1)}$$

where S refers to the stoichiometric matrix of the system, v is the flux vector. This equation simply states that over long times, the formation fluxes of a metabolite must be balanced by the degradation fluxes. Otherwise, significant amounts of the metabolite will accumulate inside the metabolic network. Applying equation 1 to our system we let S now represent the stoichiometric matrix constructed in state 18.

To completely describe the metabolic system it is necessary to include the constraints on the possible directions of the internal and exchange fluxes. The constraints on the internal fluxes is rather straightforward as all fluxes must be non-negative yielding:

$$v_i \geq 0, \forall i \quad \text{(Equation 2)}$$

where $v_i$ corresponds to the flux value of the $i^{th}$ reaction. The constraints on the exchange fluxes depend on the status of the determined source or sink on the associated metabolite, or similarly on the input and output status of the metabolite. This can be expressed in Equation 3 below where $\alpha_i$ and $\beta_i$ are either zero or negative and positive infinity, respectively, based on the direction of the exchange flux and $b_i$ corresponds to the $i^{th}$ exchange flux.

$$\alpha_i \leq b_i \leq \beta_i \quad \text{(Equation 3)}$$

Under the existence of a source(input) only $\alpha_i$ is set to negative infinity and $\beta_i$ is set to zero, whereas if only a sink(output) exists on the metabolite $\alpha_i$ is set to zero and $\beta_i$ is set to positive infinity. If both a source and sink are present then the exchange flux is bi-directional with $\alpha_i$ set to negative infinity and $\beta_i$ is set to positive infinity leaving the exchange flux unconstrained.

Together equations 1-3 describe the metabolic system under steady-state conditions as a system of linear equalities and linear inequalities. The presence of linear inequalities limits the use of traditional concepts of linear algebra, and necessitates the use of convex analysis, which is capable of treating systems of linear inequalities. The set of solutions to any system of linear inequalities included that described above is a convex space. This convex solution corresponds geometrically to a convex polyhedral cone in n-dimensional space ($R^n$) emanating from the origin for all metabolic systems modeled as described herein. We refer to this convex cone generally as the flux space and more specifically as the steady-state flux cone (C). Within this flux cone lies all of the possible solutions and hence flux distributions under which the system can operate. Since every solution or operating mode of the system is contained within the flux space, it logically follows that the entire flux space represents the capabilities of the given metabolic network. Thus the flux space clearly defines what a network can and cannot do.

Convex cones are described by the extremal rays (or generating vectors) that correspond to the edges of the cone, (being half-lines emanating form the origin). These extremal rays are said to generate the cone (forming the conical hull) and cannot be decomposed into a non-trivial convex combination of any other vectors residing in the flux cone. Here in the context of metabolic systems the term extreme pathways is used to denote the extreme rays of a polyhedral cone as each ray corresponds to a particular pathway or active set of fluxes which satisfies the steady-state mass balance constraints and inequalities of equations 1-3. Extreme pathways are denoted by the vector $p_i$ and the total number of extreme pathways needed to generate the flux cone for a system will be denoted by k. Every point within the cone (C) can be written as a non-negative convex linear combination of the extreme pathways as shown below:

$$C = v : v = \sum_{i=1}^{k} \omega_i p_i, \omega_i \geq 0 \forall i \qquad \text{(Equation 4)}$$

Thus the set of extreme pathways is analogous to a basis/coordinate system that can be used to describe a position in space. These pathways are said to conically span or generate the set of all pathways as any pathway and/or distribution of fluxes can be written as a non-negative linear combination of the $p_i$'s. The pathway vector w corresponds to the coordinate vector relative to the set of extreme pathways. It provides the weight given to each pathway in a particular flux distribution (v).

The calculation of the unique set of extreme pathways for a metabolic network, described by equations 1-3, moves the process 10 to a state 22. These pathways can be calculated using any algorithm capable of generating the conical hull of a convex polyhedral cone. One such algorithm has been previously disclosed (Schilling, 2000).

Figure 2:
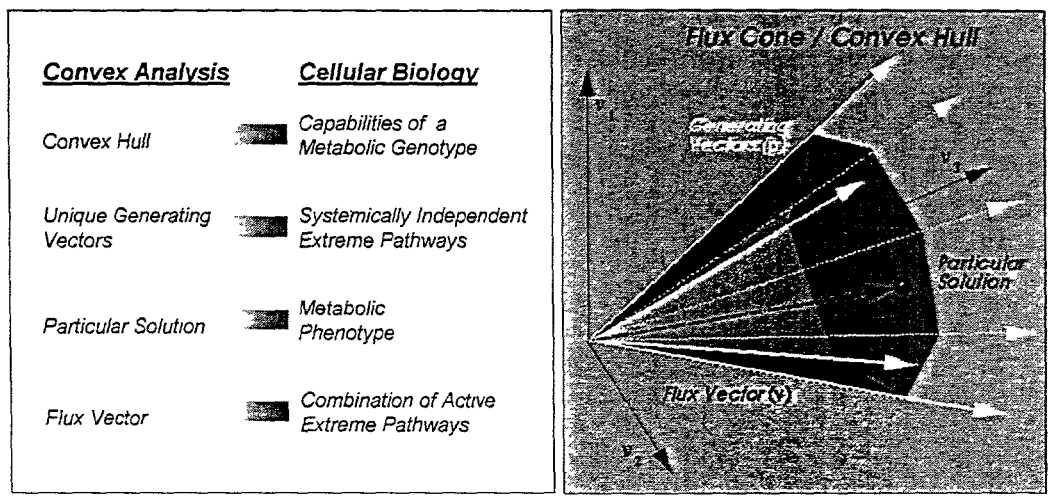
FIG. 2 is a geometric representation of the flux cone of the mathematical method of the present invention shown in three-dimensions where the entire unbounded flux cone is spanned by the generating vectors representing the capabilities of a metabolic genotype.

The set of extreme pathways geometrically represent the edges of the flux cone as depicted in FIG. 2, where the flux cone is the region of all admissible flux distributions that a metabolic network can display under the assumption of steady state. These pathways define the structural capabilities of the network and can be used to interpret every possible flux distribution or metabolic phenotype/functional modality of a metabolic network. Thus they define what a network can and cannot do; what building blocks can be produced; how efficient can the network generate biomass or extract energy from substrates; what are the redundancies in the network.

Of particular interest is the ability to use these pathways to identify critical reactions or sets of reactions that are required for the network to reach a particular objective(s). These lethal or minimal sets of reactions and the genes coding for the gene products of these reactions are herein referred to as minimal deletion sets. Furthermore, these pathways can be used to calculate every possible deletion set in a network for a given set of input and output conditions. Any combination of genetic deletions that would be lethal to an organism must contain a subset of genes that form a minimal deletion set. Therefore if the combined loss of gene A and B is lethal to an organism, where A and B alone are not essential genes, then the set is a minimal deletion set, making every superset of this also a deletion set (such as the loss of gene A, B and C).

When considering the ability of a metabolic network to produce a defined set of metabolic precursors used to generate all of the components of the biomass, these deletion sets correspond to targets or combined targets for antimicrobial therapeutics. When considering the specific production of a metabolite (i.e. amino acid) these sets correspond to reactions that can be deleted to direct the flow of metabolic resources in the cell for the metabolic engineering of an organism.

The identification of the complete group of minimal deletion sets for a metabolic network moves process 10 to a state 24. The procedure for determining a minimal deletion set follows a simple rationale. When an internal flux is eliminated from the network or identically if the flux value is forced to zero it is seen from Equation 4 that each of the pathways that utilize the particular flux are forced to be weighted to zero, otherwise non-zero values would exist in v corresponding to the eliminated reaction. Therefore all pathways that use this flux can be eliminated for further analysis of the situation. After removing the appropriate pathways, if there are no pathways capable of producing a desired output or objective then there exists no combination of pathways that can generate the particular objective. To calculate the complete group of minimal deletion sets an algorithm can be designed to check for all of the possible combinations of deletions that will eliminate all of the pathways capable of producing the desired objective.

Together the formulation of the stoichiometric matrix and reaction constraints for a metabolic network, followed by the calculation of the set of extreme pathways and lastly the identification of the entire collection of minimal deletion sets terminates the process 10 at an end state 26.

Thus by mathematically describing the reactions deemed present within a cellular metabolic network and adding or removing constraints on internal and exchange fluxes (inputs) in the network it is possible to (1) simulate a genetic deletion event or complete enzymatic inhibition and (2) simulate the presence or absence of metabolic resources available to the network perhaps to mimic its in vivo environment. Based on the resulting mathematical description of the network the unique set of extreme pathways, which define the complete range of metabolic phenotypes and production capabilities of the network, can be calculated. From these pathways particular fluxes and/or sets of fluxes can be deleted from the network to assess the ability of the network to produce the constituents of the biomass or any particular metabolic objective. If the removal of a set of internal fluxes from the network eliminates the ability of the network to produce the desired metabolic objective such as precursors for growth, and the cell can not obtain these precursors from its environment, then the removal of this set of fluxes constitutes a minimal deletion set that has potential as an antimicrobial drug target or combination of targets. All of these minimal deletion sets can be calculated based on the process described herein and the appropriate genetic targets identified from the network composition.

In addition to using these deletion sets for the identification of antimicrobial drug targets, these deletion sets can be used to design and engineer cells to have desired metabolic characteristics and capabilities that can be assessed using a pathway analysis. This has clear potential in the metabolic engineering of bacterial strains to be competitively co-cultured. Cells can thus be engineered to require specific growth environments and substrate dependencies. Opposing strains can even be designed to be co-dependent through the elimination of genes as guided by the process described herein of identifying minimal deletion sets.

It is also possible to calculate all deletion sets that will render the network to operate sub-optimally below a certain threshold from the extreme pathways, not just deletion sets that result in complete functional losses. Following the same procedure disclosed herein with only a slight modification does this calculation. Instead of looking for deletion sets that eliminate all of the pathways that generate the particular objective, only deletion set that eliminate pathways that generate the particular objective above a specified yield are calculated.

As a stoichiometric matrix or a connectivity matrix can be generated to describe biological networks in other areas such as signal transduction, the identification of minimal deletion sets is applicable for identify drug targets beyond metabolic networks, extending even into the identification of critical links or sets of points in non-biological networks.

EXAMPLE 1

Minimal Deletion Sets in a Hypothetical Reaction Network

Figure 3:
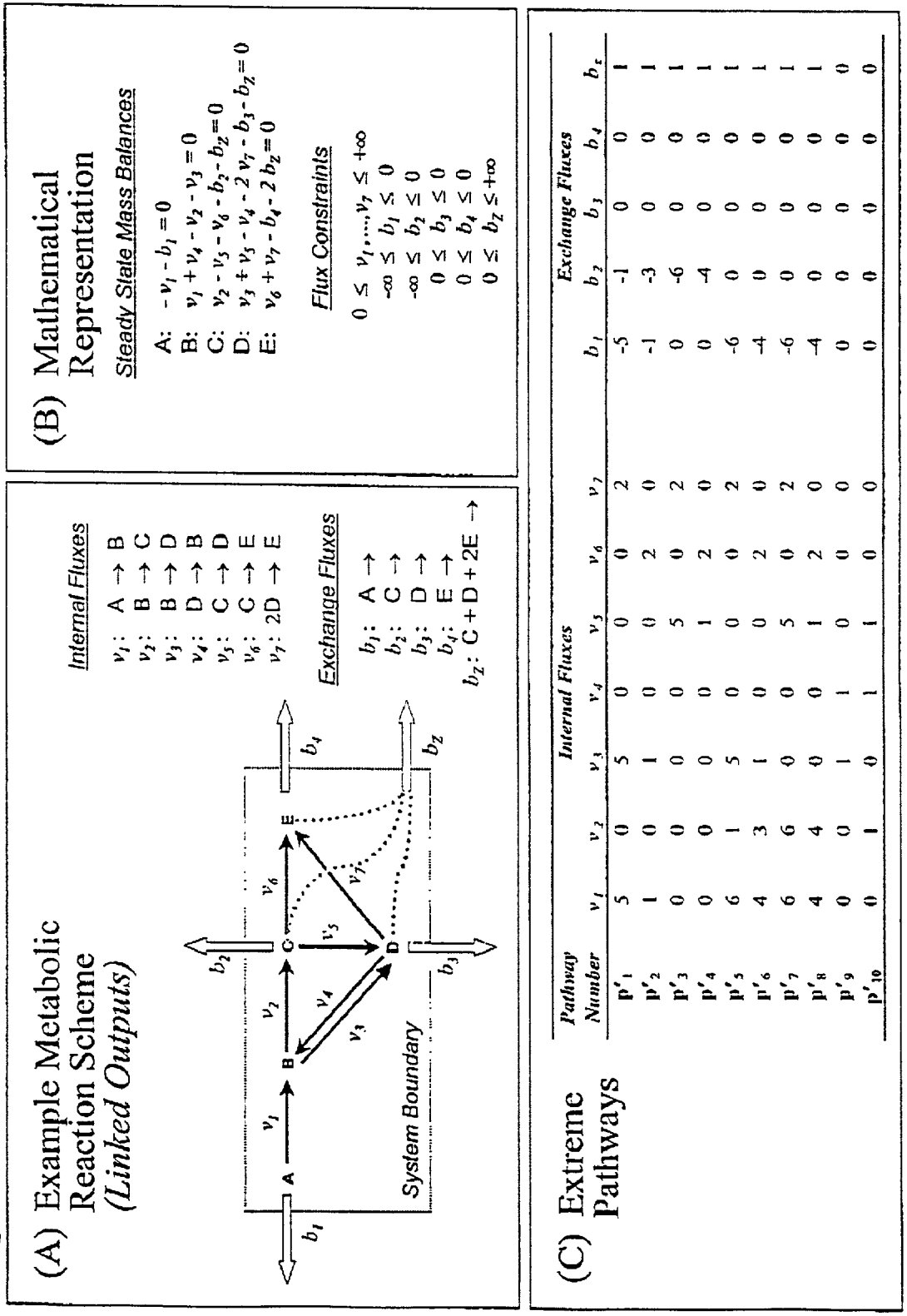
FIG. 3, consisting of FIGS. 3a-3c, are respectively a graph of an exemplary metabolic reactions scheme, a legend to the mathematical representation of the scheme, and table of the extreme pathways as collectively define a metabolic genotype and phenotype in the context of convex analysis, where, more particularly.
Figure 5:
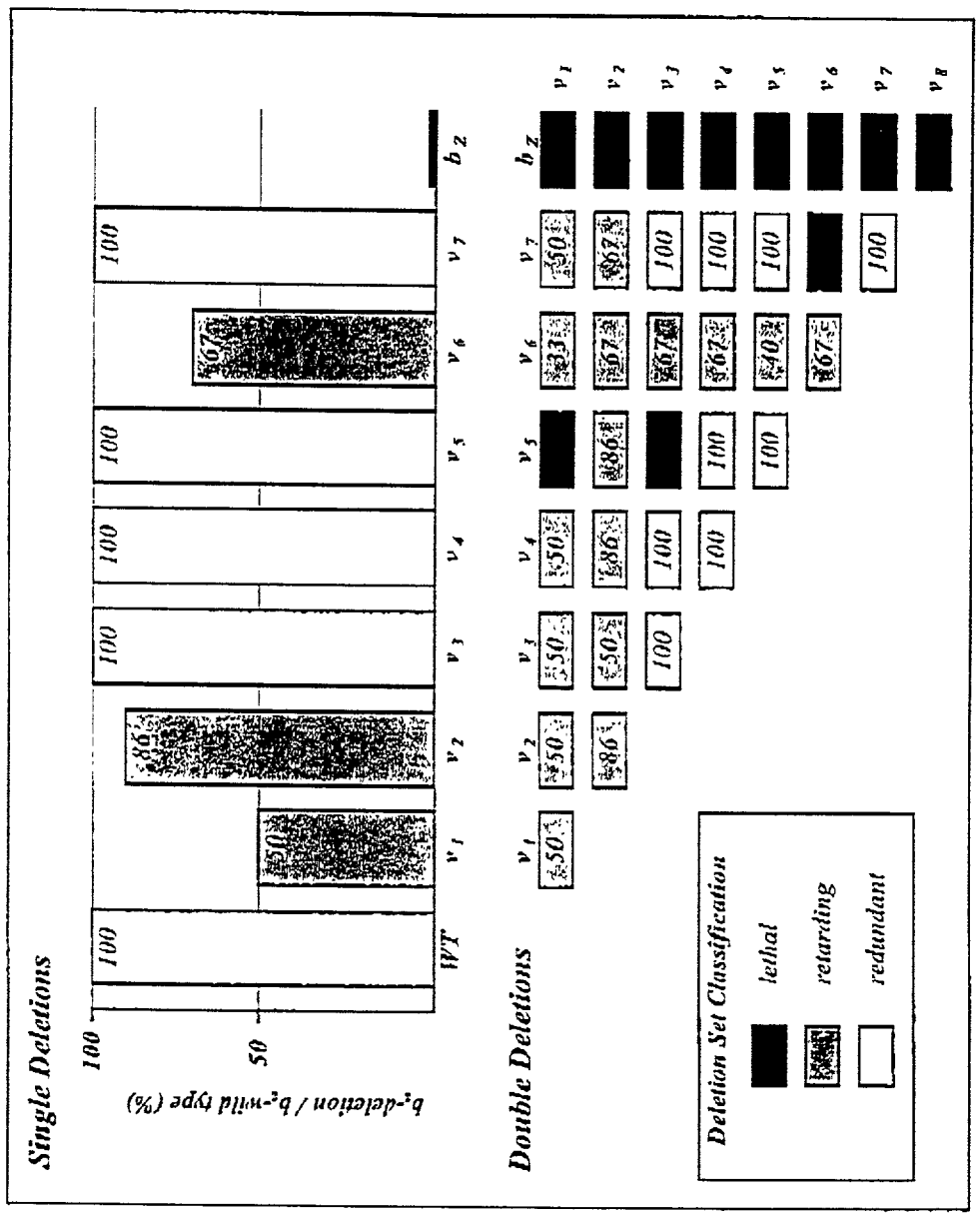
FIG. 5 is a graph showing normalized values for the objective flux ($b_z$) for all single and double deletion combinations of the network described in FIG. 3.

Using the process disclosed in FIG. 1, the entire collection of minimal deletion sets has been calculated for a hypothetical reaction network to completely illustrate the approach. The hypothetical reaction scheme considered is shown in FIG. 3(A). This network is comprised of 6 metabolites, 8 internal fluxes, and 5 exchange fluxes. Note that internal fluxes $v_3$ and $v_4$ may represent two separate reactions or be the result of a decomposition of a reversible reaction into both a forward and a reverse reaction. We will only allow metabolites A and C to enter the system as available substrates, and allow metabolite GRO to exit. GRO is a metabolite used to represent the result of a systemic demand (i.e. a growth flux, $v_z$) of one mole of C and D and 2 moles of E (analogous to biosynthetic precursors used to generate biomass or actual components of the biomass).

After determining the reactions in the network and the exchange fluxes, all of the governing mass balance equations are assembled. These equations are provided in FIG. 3(B) and can be used to generate the stoichiometric matrix for the system. In addition all of the directional constraints on the reactions, due to systems specific conditions on the input/output of various substrates and products and the thermodynamics of the internal reactions, are also provided in FIG. 3(B). The next stage in determining the minimal deletion sets for a metabolic network is the identification of the set of extreme pathways for the network. For the system provided in FIG. 3(A) the calculated extreme pathways are provided in FIG. 3(C). Pathway 1 and 2 use both A and C to reach the growth objective while pathway 3 and 4 only use C, and 5, 6, 7, and 8 use only metabolite A as their input. Pathway 9 and 10 correspond to internal cycles in the network and are ignored from further consideration, as they do not add functionality to the network. Each pathway satisfies the mass balances and flux constraints placed on the network in FIG. 3(B)

As previously mentioned when a reaction is eliminated from the network or identically if the flux value is forced to zero we can see from Equation 3 that each of the pathways that utilize the reaction are forced to be weighted to zero, otherwise non-zero values would exist in v corresponding to the eliminated reaction. Therefore all pathways that use this flux can be eliminated for further analysis of the situation. As an example consider the elimination of flux $v_1$ from the network in FIG. 3(A). We can seen from Table 1 that this would remove pathways 1, 2 and 5 through 8, leaving only pathway 3 and 4 as feasible pathways that can operate in the network. This is logical as the elimination of this particular flux would not allow metabolite A to be utilized, and subsequently all the pathways that are eliminated represent those that utilize metabolite A.

Now if we consider the case that only metabolite C is available to the network by forcing $b_1$ to equal zero, we are left once again with only pathway 3 and 4. The minimal deletion sets for growth on any particular substrate or combination of substrates corresponds to all of the sets of reactions that when deleted eliminate all of the pathways that are available to produce biomass (in our case demonstrated by a positive flux level on flux $b_3$). Thus for the situation of growth on C we can see that the elimination of fluxes $v_1$ through $v_4$ does not affect the remaining pathways ($p_3$ and $p_4$). Eliminating reaction $v_5$ and $v_8$ individually eliminates both of the remaining pathways while eliminating $v_6$ and $v_7$ together eliminate both of the pathways. Thus the minimal deletion sets for growth on substrate C is simply $\{(v_5), (v_8), (v_6,v_7)\}$. We can perform similar calculations for growth on substrate A alone by focusing on pathways 5 through 8 to reveal that the minimal deletion sets under this condition are $\{(v_1), (v_2), (v_8), (v_3,v_5), (v_6,v_7)\}$. For growth in the presence of both substrates we would have to consider all eight pathways. In this case the minimal deletion sets are $\{(v_8), (v_1,v_5), (v_3,v_5), (v_6, v_7)\}$. Thus we examine a wide range of substrate availability conditions using this approach and determine the minimal deletion sets for each particular condition. This process of determining the minimal deletion sets from a set of vectors can be easily automated on a computer to handle much larger reaction networks and sets of pathways representative of realistic cellular networks.

Linear optimization techniques such as those used in flux balance analysis (Varma, 1994, Edwards, 1999) can also be used to determine the results of all the single and double deletion combinations to confirm our results. To consider the case that both A and C are available a linear programming problem can be set up to optimize for $b_3$ while constraining the exchange fluxes for A and C not to exceed the input of more than one mole of A and one mole of C into the system. The maximum value for $b_3$ in this case would equal 0.5. From this we can compare the maximum value of $b_3$ for each single deletion and double deletion case to the "wild type" case. FIG. 4 displays the results of this type of analysis. There is no single reaction that is critical, but the combinations of $(v_1,v_5)$, $(v_3,v_5)$, and $(v_6,v_7)$ are lethal. These results are in exact agreement with minimal deletion sets calculated from the extreme pathways.

In this example the demand considered on the network was that of the GRO flux, but we could also consider a simpler case in which the demand is only one metabolite such as D or E representative of a particular cellular demand. The process is identical with the exception of the inequality constraints that are placed on the exchange fluxes before the extreme pathways are calculated.

In accordance with the preceding explanation, variations and adaptations of the mathematically based method of analyzing biochemical reaction network, also know as metabolic networks, in accordance with the present invention will suggest themselves to a practitioner of the mathematical arts.

In accordance with these and other possible variations and adaptations of the present invention, the scope of the invention should be determined in accordance with the following claims, only, and not solely in accordance with that embodiment within which the invention has been taught.

What is claimed is:

1. In a method of analyzing the production of one or more selected metabolites of a biochemical reaction network producing metabolites, the method having as inputs reactions of the biochemical reaction network constructed from genomic and biochemical data, exchange fluxes on such of the produced metabolites as are of interest as inputs and outputs to the network, a stoichiometric matrix, developed from the reactions and including the exchange fluxes, defining participation of each network metabolite in each reaction and exchange flux of the network, and a system of linear equations and inequalities mathematically defining the network, the method serving to identify deletion sets of reactions that, when removed from the network, eliminate the capability of the network to produce a selected metabolite, an improvement to the method comprising:

said linear equations and inequalities of the network mathematically forming a convex solution space called a flux cone, calculating generating vectors of the flux cone, which generating vectors are called extreme pathways;

eliminating an internal reaction flux and pathways utilizing the eliminated internal reaction flux, thereby producing an altered network, determining if said eliminated internal reaction flux diminishes the capability of the network to produce an output metabolite of interest, and providing an output of said determination to a user wherein reaction fluxes determined to diminish the capability of the network correspond to a minimal deletion set which affect the capability of the network to produce the output metabolite of interest.

2. The method according to claim 1 that further comprises:

selecting from the reaction fluxes determined to diminish the capability of the network sets of reactions that totally eliminate the capability of the network to produce the output metabolite of interest;

wherein the selected sets are called deletion sets because deletion of the reactions represented by the pathways of these sets suffices to totally eliminate the production of the output metabolite of interest by the network.

3. The method according to claim 1 wherein the calculating of the generating vectors of the flux cone is by mathematical process of convex analysis.

4. The method according to claim 3 wherein the mathematical process of convex analysis comprises: calculating any of (i) a conical basis, (ii) a convex basis, (iii) a linear basis, or (iv) a combination of any of conical and convex and linear bases.

5. The method according to claim 1 wherein at least some of the constructed reactions will have an associated constraint upon the direction in which the reaction can proceed.

6. The method according to claim 1 wherein an output of interest consists of one or more functional properties of interest of said biochemical reaction network;

wherein the reaction sets show how these one or more functional properties of interest can be diminished or eliminated.

7. The method according to claim 6 wherein the output of interest consists of one functional property of interest in the analyzed biochemical production network;

wherein the reaction sets show how this functional property of interest can be diminished or eliminated.

8. The method according to claim 1 wherein the biochemical reaction network analyzed represents a disease producing, pathogenic, organism; and wherein the metabolite of interest is necessary for survival of the pathogenic organism;

and wherein the method further comprises:

using the reaction set to target development of a drug that, by obstructing those reactions of the pathogenic organism that produce the metabolite necessary for survival of the organism, serves to eliminate the pathogenic organism.

9. The method according to claim 1 wherein the biochemical reaction network analyzed represents a disease producing, pathogenic, organism; and wherein the metabolite of interest, produced by the pathogenic organism, is deleterious, inducing disease; and wherein the method further comprises:

using the reaction set for targeting the development of a drug that, by obstructing those reactions of the pathogenic organism that produce the metabolite that induces disease, serves to eliminate the deleterious, disease-causing, function of the pathogenic organism.

10. The method according to claim 1 wherein the reaction network analyzed represents an organism producing desired bio-molecules of value and undesired bio-molecules of no value; and wherein the metabolite of interest produced by the organism is the undesired valueless bio-molecules;

and wherein the method further comprises:

using the reaction set to metabolically re-engineer the organism to fail in those reactions that produce the metabolite that is undesired and valueless, therein eliminating production of undesired valueless bio-molecules while permitting production of desired valued bio-molecules.

11. The method according to claim 1 wherein the reaction network analyzed represents an organism producing desired bio-molecules of value by multiple metabolic routes; and wherein the metabolite of interest is produced by one of the routes of the organism; and wherein the method further comprises:

using the reaction set to metabolically re-engineer the organism to fail in those reactions that produce the metabolite of interest via the one route, therein by eliminating production of metabolite via this route, nonetheless that the metabolite is of value, leaving intact production of the same metabolite by alternative ones of the multiple metabolic routes.

* * * * *